United States Patent [19]

Szilagyi et al.

[11] 4,251,658
[45] Feb. 17, 1981

[54] 3-(1-PYRAZOLYL)-PYRIDAZINE DERIVATIVES

[75] Inventors: Géza Szilágyi; Endre Kasztreiner; László Tardos; Edit Kosa; László Jaszlits; György Cseh; András Divald; Pál Tolnay; Sándor Elek; István Elekes; István Polgári, all of Budapest, Hungary

[73] Assignee: Richter Gedeon Vegyeszeti Gyar Rt., Budapest, Hungary

[21] Appl. No.: 914,084

[22] Filed: Jun. 9, 1978

[30] Foreign Application Priority Data

Jun. 13, 1977 [HU] Hungary ................ GO 1373

[51] Int. Cl.³ ............... C07D 403/04; C07D 401/14; C07D 405/14; A61K 31/50
[52] U.S. Cl. ........................ 544/238; 424/250; 424/248.54; 424/248.55; 424/248.53; 544/114
[58] Field of Search ............... 424/250; 544/238

[56] References Cited

U.S. PATENT DOCUMENTS 3,367,936 2/1968 Koppe et al. .................. 544/238

OTHER PUBLICATIONS

Shirakawa et al., Chem. Abs. 60, 12009–12011, (1964).
Elguero et al., Bul. Chem. Soc., France, 1970, 1346.
Twomey, Chem. Abs., 81, 3864t, (1974).
Elguero et al., Bull. Soc. Chim. Fr., 1970, p. 1346.
Shirakawa et al., Chem. Abs., 60, 12010, (1963).
Karpova et al., Chem. Abs., 81, 3864, (1974).

Primary Examiner—Mark L. Berch

Attorney, Agent, or Firm—Karl F. Ross

[57] ABSTRACT 3-(1-Pyrazolyl)-pyridazine derivatives of the formula I, or pharmaceutically acceptable acid addition salts thereof, which decrease high blood pressure and inhibit catabolism or prostaglandins,

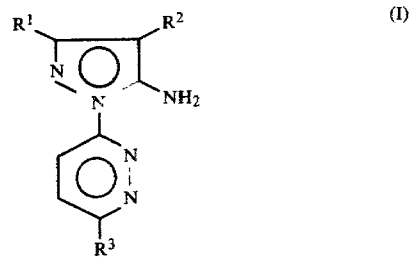

wherein
$R^1$ is hydrogen or $C_{1-4}$ alkyl,
$R^2$ is hydrogen, cyano, carboxyl, carbamoyl, carbaxoyl or $C_{1-4}$ alkoxycarbonyl,
$R^3$ is hydrogen or chlorine or $-NR^4NHR^5$ or $NR^6R^7$, wherein $R^4$ and $R^5$ are each hydrogen or $C_{1-4}$ alkyl, wherein $R^6$ and $R^7$ are each hydrogen or $C_{1-5}$ alkyl, $C_{1-5}$ hydroxyalkyl, $C_{3-7}$ cycloalkyl, phenyl or benzyl, or benzyl or phenylethyl substituted with one or two chlorine atoms or methoxy groups, or a furylmethyl, pyridylmethyl, pyrrolidine or piperazine ring, or when $R^7$ is hydrogen, $R^6$ is $-(CH_2)_n-NR^4R^5$ wherein n is an integer from 1 to 3.

3 Claims, No Drawings

3-(1-PYRAZOLYL)-PYRIDAZINE DERIVATIVES

This invention relates to new 3-(1-pyrazolyl)-pyridazine derivatives to their pharmaceutically acceptable salts and to compositions containing them.

It is well known that one of the most dangerous forms of hypertensive condition is so-called renal hypertension arising from renal insufficiency which is characterized, on the one hand, by constriction of the blood vessels of kidney and, on the other hand, according to recent investigations, by the decreased prostaglandin content of blood-vessel walls of the kidney (Circ. Res. 36–37, Suppl. I., pp. 68 and 81 (1975) which is in a closely related to the process of constriction.

Now it has been found that the new 3-(1-pyrazolyl)-pyridazine compounds of formula I possess a significant hypotensive effect and are capable of significant inhibition of enzymes (prostaglandin dehydrogenase and prostaglandin-A isomerase) regulating the catabolism of prostaglandins which results in an increase in the endogenous prostaglandin levels.

Accordingly the invention relates to new 3-(1-pyrazolyl)-pyridazine derivatives of the formula I

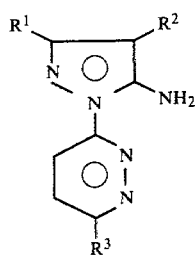

wherein
- $R^1$ is hydrogen or $C_{1-4}$ alkyl,
- $R^2$ is hydrogen, cyano, carboxyl, carbamoyl, carbazoyl or $C_{1-4}$ alkoxycarbonyl,
- $R^3$ is hydrogen or chlorine or an $-NR^4-NHR^5$ group or $NR^6R^7$, wherein $R^4$ and $R^5$ stand independently from each other for a hydrogen atom or a $C_{1-4}$ alkyl, wherein $R^6$ and $R^7$ are independently from each other either hydrogen or $C_{1-5}$ alkyl, $C_{1-5}$ hydroxyalkyl, $C_{3-7}$ cycloalkyl, phenyl or benzyl, or a benzyl or phenylethyl group substituted by one or two chlorine atoms or methoxy groups, or a furylmethyl, pyridylmethyl, pyrrolidine or piperazine ring, or when $R^7$ is hydrogen, $R^6$ represents $-(CH_2)_n-NR^4R^5$, wherein n represents and integer from 1 to 3, and their pharmaceutically acceptable acid-addition salts.

In the compounds of formula I, $R^1$ preferably is hydrogen, $R^2$ can be ethoxycarbonyl, cyano or carbamoyl and $R^3$ can be hydrazino, cyclopropylamino or benzylamino.

The compounds of formula I can be prepared according to the invention by reacting a compound of formula II

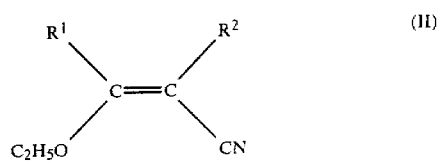

wherein $R^1$ has the same meaning as above and $R^2$ is cyano group or $C_{1-4}$ alkoxycarbonyl group, with a compound of formula III

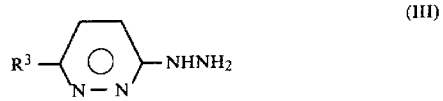

wherein $R^3$ is hydrogen or chlorine, and by reacting, if desired, the compound of formula I so obtained with a hydrazine of the formula $R^4NHNHR^5$, with an amine of the formula $HNR^6R^7$ and, if desired, hydrolyzing the compound of formula I so obtained to an acid amide or acid when $R^2$ stands for a cyano group, or reacting it with hydrazine or hydrolyzing it to an acid when $R^2$ stands for $C_{1-4}$ alkoxycarbonyl and, if desired, by decarboxylating the compound of formula I so obtained, wherein $R^1$ and $R^3$ have the same meaning as above, whereas $R^2$ stands for a carboxyl group and, if desired, converting the free base of formula I so obtained into a pharmaceutically acceptable acid-addition salt, or converting an acid-addition salt into the free base.

The compounds of formula II are preferably reacted with compounds of formula III by using lower alcohols as solvents, advantageously at a temperature between 50° C. and 120° C. Subsequently the chlorine atom present in the pyridazine moiety of the thus-obtained compound of formula I is brought to reaction with a hydrazine of formula $NHR^4-NHR^5$ or with an amine of formula $NHR^6R^7$, in or without a solvent, suitably at a temperature between 50° C. and 180° C. Polar substances, e.g. dimethylformamide or dimethyl sulphoxide, are quite convenient as solvents.

A large number of part of the compounds of formula II are known in the literature (Beilstein's Handbuch der Organischen Chemie 3, 470 (Ed. Julius Springer, Berlin, 1921) and ibid. I. Ergäanzungswerk 3, 162 (Ed. Julius Springer, Berlin, 1929), and can be prepared by the reaction of malonicnitrile or cyanoacetic acid esters, respectively, with an orthoacid ester.

Of the compounds of formula III, 3-pyridazinylhydrazine and 3-chloro-6-pyridazinylhydrazine are known in the literature [Yakugaku Zasshi 75, 778 (1955); Chemical Abstr. 50, 4970b (1956)].

The acid amides of formula I are conveniently prepared by partial hydrolysis of the corresponding nitriles, suitably by means of sulphuric acid, at a temperature between 0° C. and 30° C.

The carboxylic acid esters of formula I are conveniently transformed to hydrazides by using an excess of hydrazine in a lower aliphatic alcohol as solvent, suitably at boiling temperature of the alcoholic solvent.

The carboxylic acids of formula I are conveniently prepared by alkaline hydrolysis of the corresponding esters. The hydrolysis is preferably carried out by a solution of sodium hydroxide or potassium hydroxide in a lower aliphatic alcohol containing water, at the boiling point of the solvent.

The compounds of formula I, wherein $R^2$ is hydrogen, are prepared from the acids of general formula I, preferably by thermal decarboxylation or by the simultaneous hydrolysis and decarboxylation with 48% hydrobromic acid of the corresponding esters, suitably at the boiling point of the reaction mixture.

The acid-addition salts of the compounds of formula I can conveniently be prepared in the following way. The base of formula I is dissolved e.g. in methanol, ethanol, isopropanol or ether, and to this mixture the solution of the desired inorganic acid in methanol, ethanol or ether or the solution of the desired organic acid in methanol, ethanol, isopropanol, ether or acetone, respectively, is added dropwise under cooling. The precipitated product is separated by filtration and recrystallized, if desired.

Hydrochloric, hydrobromic, sulphuric or phosphoric acid can conveniently be used as inorganic acids. The use of tartaric, maleic, fumaric, methanesulphonic, ethanesulphonic or 4-toluenesulphonic acid is suitable as organic acids.

The hypotensive action of the compounds according to the invention was demonstrated in cats of both sexes weighing 2 to 4 kg, narcotized intraperitoneally by 30 mg/kg of Pentobarbital (L. A. Geddes: The Direct and Indirect Measurement of Blood Pressure, Year Book Medical Publishers, Chicago 1970). The substances were administered in doses of 5, 2.5 and 1 mg./kg., respectively, and Hydralazine (1-hydrazinophthalazine hydrochloride) was used as reference compound. The hypotensive action of several substances is shown in Table I.

TABLE I

| No. of Example | Decrease in blood pressure in Hgmm by 1 mg./kg. | Acute oral toxicity on mice $LD_{50}$ in mg./kg. |
| --- | --- | --- |
|  | −15 | 000 |
| 0 | −40 | 200 |
| 1 | −10 | 250 |
| 2 | −10 | 200 |
| 3 | −10 | −150 |
| Hydralazine | −40 | 200 |

The hypotensive action of substance 30 was studied also in spontaneously hypertensive (Wistar-Okamoto) rats (Arzneim.-forsch. 6, 222 (1956): the systolic blood pressure was measured in the caudal artery by an indirect method, after oral treatment. In a dose of 20 mg./kg., substance 30 caused a decreased of 31% in blood pressure after 2 hours, 16% after 5 hours and 15% after 24 hours, respectively. Hydralazine used as reference compound in a dose of 10 mg./kg. resulted in a decrease of 21, 22 and 15%, respectively, after the same time periods. An advantageous property against Hydralazine of substance 30 is that it does not cause any significant tachycardia.

The prostaglandin-A isomerase (PGAI) inhibiting action of the compounds according to the invention was measured by the method of Jones et al. (Biochim. Biophys. Acta 280, 558 (1972) on a PGAI preparation from the blood-plasma of pigs, whereas the prostaglandin dehydrogenase (PGDH) inhibiting action was determined by the method of Marrazzi and Matschinsky (Prostaglandins 1, 373 (1972) on a PGDH preparation from pig-lung. The PGAI and PGDH inhibiting action of several substances is shown in Table II.

TABLE II

| No. of Examples | $I_{50\%}$ inhibiting levels in final concentrations expressed in millimoles | |
| --- | --- | --- |
|  | PGDH | PGAI |
| 5 | 0 | 0.10 |
| 6 | 0.055 | 0.05 |
| 11 | 0 | 0.044 |
| 16 | 0.15 | 0.075 |
| 17 | 0.20 | 0.025 |
| 18 | 0 | 0.036 |
| 20 | 0 | 0.18 |
| 38 | 0.045 | 0.025 |
| 40 | 0 | 0.075 |
| Hydralazine | — | 0.09 |
| Estrone | 0.01 | — |
| Triiodothyroacetic acid | 0.005 | — |

The $I_{50\%}$, i.e. the index of inhibition is defined as the concentration of the substance inhibiting to 50% the function of the corresponding enzyme.

The process according to the invention is further illustrated by means of the following Examples.

EXAMPLE 1

Preparation of 3-(4-methyl-1-piperazino)-6-(4-ethoxycarbonyl-5-amino-1-pirazolyl)-pyridazine A mixture of 5.36 g. (20 mmoles) of 3-chloro-6-(4-ethoxycarbonyl-5-amino-1-pyrazolyl)-pyridazine and 4.4 g. (44 mmoles) of 1-methylpiperazine is heated at 150° C. for 6 hours, and after cooling the mixture is triturated with water, filtered and recrystallized from ethanol. Yield: 4.8 g (73.5%); m.p.: 150°–151° C.

The substances of formula I prepared by the above procedure and their acid addition salts are shown in Table III.

TABLE III

| No. of Example | Chemical name of the compound | Melting point °C. | Yield** % |
| --- | --- | --- | --- |
| 2 | 3-bis(Hydroxyethyl)amino-A | 144–6 | 42.5 |
| 3 | 3-Hydroxyethylamino-A | 191–3 168–170* | 76 |
| 4 | 3-(3,4-Dimethoxyphenylethyl-amino)-A | 126–7 189–192* | 69.5 |
| 5 | 3-Cyclohexylamino-A | 171–3 | 96 |
| 6 | 3-Furfurylamino-A | 161–4 175–8* | 52.5 |
| 7 | 3-Benzylamino-A | 135–7 200–3* | 62.5 |
| 8 | 3-Morpholino-A | 172–5 175–6* | 83 |
| 9 | 3-(Cyclopropylamino)-A | 167–170 215–217* | 64 |
| 10 | 3-(4-Hydroxyethyl-1-piperazino)-A | 141–3 | 73 |
| 11 | 3-(2-Diethylaminoethylamino)-A | 108–110 | 62.5 |
| 12 | 3-Phenylethylamino-A | 146–7 176–9* | 49 |
| 13 | 3-(4-Chlorobenzylamino)-A | 160–2 206–8* | 84.5 |
| 14 | 3-Cyclohexylmethylamino-A | 174–6 198–200* | 71.5 |
| 15 | 3-Anilino-A | 250–2 249–251* | 62 |
| 16 | 3-(2Pyridylmethylamino)-A | 155–8 198–200* | 52 |
| 17 | 3-(3-Pyrdiylmethylamino)-A | 163–5 190–1(d)* | 72 |
| 18 | 3-(4-Pyridylmethylamino)-A | 135–7 165–8* | 71 |
| 19 | 3-(4-Methoxybenzylamino)-A | 187–190 207–210* | 62.5 |

TABLE III-continued

| No. of Example | Chemical name of the compound | Melting point °C. | Yield** % |
|---|---|---|---|
| 20 | 3-(1-Phenylethylamino)-A | 159-160 209-212* | 30.5 |
| 21 | 3-(1-Ethyl-2-pyrrolidinyl-methylamino)-A | 192-5 | 68 |

Notes to Table III:
A: 6-(4-Ethoxycarbonyl-5-amino-1-pyrazolyl)-pyridazine
*hydrochloride salt
**preparative yields (after recrystallisation)
d: decomposition

EXAMPLE 22

Preparation of 3-chloro-6-(4-cyano-5-amino-1-pyrazolyl)pyridazine

A mixture of 4.35 g. (30 mmoles) of 3-chloro-6-pyridazinylhydrazine, 3.96 g. (30 mmoles) of ethoxymethylenemalononitrile and 60 ml. of ethanol is heated and refluxed for 2 hours. After cooling the separated crystals are filtered, washed with ethanol and dried. Yield: 5.85 g. (88.5%); m.p.: 250°-252° C.

The substances of formula I prepared by the above procedure are shown in Table IV.

TABLE IV

| No. of Example | Chemical name of the compound | Melting point °C. | Yield* % |
|---|---|---|---|
| 23 | 3-Chloro-6-(3-methyl-4-cyano-5-amino-1-pyrazolyl)-pyridazine | 296-299 | 77.5 |

Note to Table IV:
*preparative yields (after recrystallisation)

EXAMPLE 24

Preparation of 3-chloro-6-(4-carbamoyl-5-amino-1-pyrazolyl)-pyridazine

A mixture of 3 g. of 3-chloro-6-(4-cyano-5-amino-1-pyrazolyl)-pyridazine (prepared according to Example 24) and 10.5 ml. of concentrated sulphuric acid is stirred at room temperature for one hour. Then the mixture is poured onto ice, the precipitate filtered, washed with water and triturated with 15 ml. of hot ethanol, filtered and dried. Yield: 3.05 g. (93.5%); m.p.: 314°-317° C.

EXAMPLE 25

Preparation of 3-(4-carbamoyl-5-amino-1-pyrazolyl)-pyridazine

This compound is prepared by the process described in Example 24. Yield: 65.5%; m.p.: 295°-298° C.

EXAMPLE 26

3-Hydrazino-6-(4-cyano-5-amino-1-pyrazolyl)-pyridazine

A mixture of 10 g. of 3-chloro-6-(4-cyano-5-amino-1-pyrazolyl)-pyridazine (prepared according to Example 24), 20 ml. dimethylformamide and 40 ml. of 98% hydrazine hydrate is heated at 90°-95° C. for 5 hours. After cooling the precipitated product is filtered, washed with water and ethanol, triturated with 50 ml. of hot ethanol, filtered and dried. Yield: 9.1 g. (93%); m.p.: 264°-266° C. The hydrochloride melts at 253°-256° C.

The substances of formula I prepared by the above procedure and their acid addition salts are shown in Table V.

TABLE V

| No. of Example | Chemical name of the compound | Melting point °C. | Yield** % |
|---|---|---|---|
| 27 | 3-Hydrazino-6-(4-ethoxycarbonyl-5-amino-1-pyrazolyl)-pyridazine | 190-192 | 96 |
| 28 | 3-Hydrazino-6-(3-methyl-4-cyano-5-amino-1-pyrazolyl)-pyridazine | 252-255 284-286* | 78.5 |
| 29 | 3-Hydrazino-6-(4-carbamoyl-5-amino-1-pyrazolyl)-pyridazine | 248-250 262-265* | 37.5 |

Notes to Table V:
*hydrochloride salt
**preparative yields (after recrystallisation)

EXAMPLE 30

Preparation of 3-(1-methylhydrazino)-6-(4-cyano-5-amino-1-pyrazolyl)-pyridazine

A mixture of 2.2 g. (10 mmoles) of 3-chloro-6-(4-cyano-5-amino-1-pyrazolyl)-pyridazine (prepared according to Example 24), 1.38 g. (30 mmoles) of methylhydrazine and 25 ml. of dimethylformamide is heated at 120°-130° C. for 7.5 hours, and after cooling the mixture is poured onto ice. The separated crystals are filtered, washed with water and triturated with 5 ml. of hot ethanol, filtered and dried. Yield: 2.1 g. (91%); m.p.: 260° C. (with decomposition).

EXAMPLE 31

3-[bis(2-Hydroxyethyl)-amino]-6-(4-carbazoyl-5-amino-1-pyrazolyl)-pyridazine

A mixture of 6.72 g. (20 mmoles) of 3-[bis(hydroxyethyl)-amino]-6-(4-ethoxycarbonyl-5-amino-1-pyrazolyl)-pyridazine (prepared according to Example 2), 34 ml. of 72% hydrazine hydrate and 34 ml. of dioxane is stirred at reflux temperature for 12 hours. After cooling the separated crystals are filtered, washed with water and ethanol and then recrystallized from 30 ml. of ethanol. Yield: 5.7 g. (88.5%); m.p.: 217°-219° C.

The substances of formula I prepared by the above procedure and their acid addition salts are shown in Table VI.

TABLE VI

| No. of Example | Chemical name of the compound | Melting point °C. | Yield** % |
|---|---|---|---|
| 32 | 3-(4-Carbazoyl-5-amino-1-pyridazine | 254-256 | 89 |
| 33 | 3-(3,4-Dimethoxyphenylethyl-amino)-B | 195-198 | 54 |
| 34 | 3-Benzylamino-B | 175-178 | 76.5 |
| 35 | 3-(3-Pyridylmethylamino)-B | 221-222 258-260* | 58.5 |
| 36 | 3-(2-Furylmethylamino)-B | 214-215 212-214*** | 87 |

Notes to Table VI:
6-(4-Carbazoyl-5-amino-pyrazolyl)-pyridazine
*hydrochloride salt
**preparative yields (after recrystallisation)
***:dihydrochloride salt

EXAMPLE 37

Preparation of 3-hydrazino-6-(4-carbazoyl-5-amino-1-pyrazolyl)-pyridazine

A mixture of 3 g of 3-chloro-6-(4-ethoxycarbonyl-5-amino-1-pyrazolyl)-pyridazine, 30 ml. of 72% hydrazine hydrate and 40 ml. of dioxane is stirred at reflux temperature for 24 hours. After cooling the separated crystals are filtered, washed with water and ethanol, triturated with hot ethanol, filtered and dried. Yield: 2.0 g. (77%); m.p.: 302°–305° C.

EXAMPLE 38

Tablets containing 200 mg. of active ingredient each, for oral use and therapeutic purposes are prepared from the following components:

| | |
|---|---|
| 3-Hydrazino-6-(4-cyano-5-amino-1-pyrazolyl)-pyridazine | 200 mg. |
| Microcrystalline cellulose | 46.4 mg. |
| Colloidal silicium dioxide | .8 mg. |
| Magnesium stearate | .8 mg. |

The average weight of one tablet is 350 mg.

The tablets are covered with film coat.

Preparation of an injectable product:

For parenteral use, a sterile, frozen-dried product containing in each ampoule 25 mg. of 3-hydrazino-6-(4-cyano-5-amino-1-pyrazolyl)-pyridazine hydrochloride is prepared from the solution of the compound (in injectable distilled water).

In order to prepare the hydrochlorides of compounds described in the Examples, the base is suspended in ether or ethanol and saturated with gaseous hydrogen chloride. In some cases it is satisfactory to add ethanolic hydrochloric acid to the ethereal or ethanolic suspension of the base. The precipitate is filtered, washed with ether and dried. The melting point data of the hydrochlorides so obtained are shown in the above Tables.

What we claim is:

1. A compound of the formula:

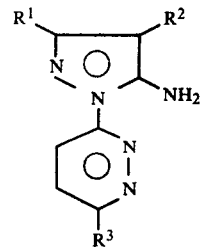

wherein
   $R^1$ is hydrogen or $C_1$ to $C_4$ alkyl;
   $R^2$ is cyano, carboxyl, carbamoyl, carbazoyl, or $C_1$ to $C_4$ alkoxycarbonyl; and
   $R^3$ is —NR$^4$—NHR$^5$ or —NR$^6$R$^7$ wherein
      $R^4$ and $R^5$ are each independently hydrogen or $C_1$ to $C_4$ alkyl;
      $R^6$ and $R^7$ are each independently hydrogen, $C_1$ to $C_5$ alkyl, $C_1$ to $C_5$ hydroxyalkyl, $C_3$ to $C_7$ cycloalkyl, phenyl, benzyl, benzyl or phenethyl substituted by one or two chlorine atoms or methoxy groups, furylmethyl, or pyridylmethyl; or
      $R^7$ is hydrogen and $R^6$ is —(CH$_2$)$_n$—NR$^4$R$^5$ wherein n is an integer from 1 to 3;
or a pharmaceutically acceptable salt thereof.

2. The compound defined in claim 1 selected from the group consisting of:
   3-cyclohexylamino-6-(4-ethoxycarbonyl-5-amino-1-pyrazolyl)-pyridazine;
   3-furfurylamino-6-(4-ethoxycarbonyl-5-amino-1-pyrazolyl)-pyridazine;
   3-benzylamino-6-(4-ethoxycarbonyl-5-amino-1-pyrazolyl)-pyridazine;
   3-(2-diethylaminoethylamino)-6-(4-ethoxycarbonyl-5-amino-1-pyrazolyl)-pyridazine;
   3-(2-pyridylmethylamino)-6-(4-ethoxycarbonyl-5-amino-1-pyrazolyl)-pyrazine;
   3-(3-pyridylmethylamino)-6-(4-ethoxycarbonyl-5-amino-1-pyrazolyl)-pyridazine;
   3-(4-pyridylmethylamino)-6-(4-ethoxycarbonyl-5-amino-1-pyrazolyl)-pyridazine;
   3-hydrazino-6-(4-cyano-5-amino-1-pyrazolyl)-pyridazine;
   3-hydrazino-6-(4-ethoxycarbonyl-5-amino-1-pyrazolyl)-pyridazine;
   3-hydrazino-6-(3-methyl-4-cyano-5-amino-1-pyrazolyl)-pyridazine;
   3-hydrazino-6-(4-carbamoyl-5-amino-1-pyrazolyl)-pyridazine;
   3-benzylamino-6-(4-carbazoyl-5-amino-1-pyrazolyl)-pyridazine; and
   3-(2-furylmethylamino)-6-(4-carbazoyl-5-amino-1-pyrazolyl)-pyridazine;
or a pharmaceutically acceptable salt thereof.

3. The compound defined in claim 1 which is 3-hydrazino-6-(4-cyano-5-amino-1-pyrazolyl)-pyridazine or a pharmaceutically acceptable acid addition salt thereof.